United States Patent [19]

Butler et al.

[11] Patent Number: 5,155,251
[45] Date of Patent: Oct. 13, 1992

[54] PROCESS FOR THE SYNTHESIS OF (5R)-1,1-DIMETHYLETHYL 6-CYANO-5-HYDROXY-3-OXO-HEXANOATE

[75] Inventors: Donald E. Butler, Holland; Tung V. Le, Jenison; Alan Millar; Thomas N. Nanninga, both of Holland, all of Mich.

[73] Assignee: Warner-Lambert Company, Morris Plains, N.J.

[21] Appl. No.: 775,162

[22] Filed: Oct. 11, 1991

[51] Int. Cl.$^5$ .......................................... C07C 253/30
[52] U.S. Cl. .................................. 558/442; 558/347; 558/342
[58] Field of Search ........................................ 558/442

[56] References Cited

U.S. PATENT DOCUMENTS

| | | | |
|---|---|---|---|
| 4,647,576 | 3/1987 | Hoefle et al. | 514/422 |
| 4,681,893 | 7/1987 | Roth | 514/422 |
| 5,003,080 | 3/1991 | Butler et al. | 548/517 |

OTHER PUBLICATIONS

Migrdichian, "The Chemistry of Organic Cyanogen Compounds", (1947), pp. 125–132; Reinhold Pub. Co., N.Y.

Primary Examiner—Joseph Paul Brust
Attorney, Agent, or Firm—Francis J. Tinney

[57] ABSTRACT

An improved process for the preparation of (5R)-1,1-dimethylethyl 6-cyano-5-hydroxy-3-oxo-hexanoate is described where a halo hydroxyester or other activated dihydroxyester is converted in two steps to the desired product.

8 Claims, No Drawings

PROCESS FOR THE SYNTHESIS OF (5R)-1,1-DIMETHYLETHYL 6-CYANO-5-HYDROXY-3-OXO-HEXANOATE

BACKGROUND OF THE INVENTION (4R-Cis)-1,1 dimethylethyl 6-(2-aminoethyl)-2,2-dimethyl-1,3-dioxan-4-acetate is a key intermediate in the preparation of (2R-trans)-5-(4-fluorophenyl)-2-(1-methylethyl)-N,4-diphenyl]-1-[2-(tetrahydro-4-hydroxy-6-oxo-2H-pyran-2-yl)ethyl]-1H-pyrrole-3-carboxamide or the salt of the hydroxy acid, [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1), corresponding to the opened lactone ring of the aforementioned compound described in U.S. Pat. Nos. 4,647,576 and 4,681,893, which are herein incorporated by reference. The aforementioned compound is useful as an inhibitor of the enzyme 3-hydroxy-3-methylglutaryl-Coenzyme A reductase (HMG-CoA reductase) and is thus useful as a hypolipidemic and hypocholesterolemic agent.

(4R-Cis)-1,1-dimethylethyl 6-(2-aminoethyl)-2,2-dimethyl-1,3-dioxane-4-acetate may be, in turn, prepared from (4R-Cis)-1,1-dimethylethyl 6-cyanomethyl-2,2-dimethyl-1,3-dioxane-4-acetate which may, in turn, be prepared from (5R)-1,1-dimethylethyl 6-cyano-5-hydroxy-3-oxo-hexanoate.

A synthetic procedure for preparing (5R)-1,1-dimethylethyl 6-cyano-5-hydroxy-3-oxo-hexanoate is disclosed in U.S. Pat. No. 5,003,080. The aforementioned procedure involves a linear synthetic route involving 5 steps, involving use of protected intermediates. Although this procedure provides the target compound it is difficult to conduct on large scale, requires use of expensive starting materials, and involves the use of costly protecting group and deprotecting group reagents in the process.

There are several literature reports in which the anion of tertiary butyl acetate is reacted with a 3-hydroxy ester in the desired manner to afford a β-keto-δ ester, for example, Lynch, J. E., et al, *Tetrahedron Letters*, Volume 23, pages 1385-1388 (1987) and U.S. Pat. No. 4,970,313. However, none of the known examples contain a nitrile group. Moreover, U.S. Pat. No. 4,983,759 discloses the reaction of a nitrile with the anion of tertiary butyl acetate resulting in reaction at the nitrile end of the molecule.

Thus, we have surprisingly and unexpectedly found that the reaction of the anion of tertiary butyl acetate with (3R)-4-cyano-3-hydroxybutyric acid esters proceeds very efficiently to afford the desired compound, (5R)-1,1-dimethylethyl 6-cyano-5-hydroxy-3-oxo-hexanoate.

The object of the present invention is an improved, short, efficient, and economical process for the preparation of (5R)-1,1-dimethylethyl 6-cyano-5-hydroxy-3-oxo-hexanoate. Thus, the present method avoids costly starting materials, protection and deprotection of intermediates of the prior method and is amenable to large scale synthesis.

SUMMARY OF THE INVENTION

Accordingly, a first aspect of the present invention is an improved process for the preparation of the compound of Formula I

which comprises:
(a) treating a compound of Formula V

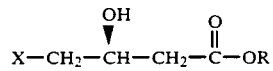

wherein R is alkyl of from one to ten carbon atoms, allyl, or benzyl and X is a leaving group with a compound of Formula IV

wherein $R^1$ is tetraalkylammonium, silver, copper (I), copper (II), an alkali metal, or an alkaline earth metal in a solvent at about 0° C. to about the reflux temperature of the solvent to afford a compound of Formula II

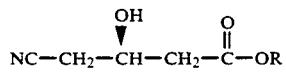

wherein R is as defined above or optionally treating a compound of Formula VI

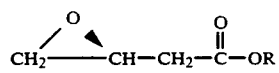

wherein R is as defined above with a compound of Formula IV in a solvent at about 0° C. to about the reflux temperature of the solvent to afford a compound of Formula II; and (b) treating a compound of Formula II with a compound of Formula III

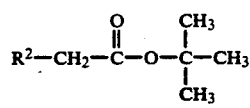

wherein $R^2$ is zinc, magnesium or lithium and a solvent at about −80° C. to about room temperature to afford the compound of Formula I.

A second aspect of the present invention is an improved process for the preparation of a compound of Formula II

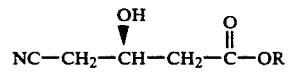

wherein R is alkyl of from one to ten carbon atoms, allyl, or benzyl which comprises:
treating a compound of Formula V

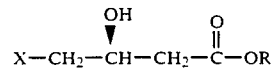

wherein X is a leaving group and R is as defined above with a compound of Formula IV $R^1-CN$  IV wherein $R^1$ is tetraalkylammonium, silver, copper (I), copper (II), an alkali metal or an alkaline earth metal in a solvent at about 0° C to about the reflux temperature of the solvent to afford a compound of Formula II.

DETAILED DESCRIPTION OF THE INVENTION

In this invention the term "alkyl" means a straight or branched hydrocarbon radical having from one to ten carbon atoms and includes, for example, methyl, ethyl, n-propyl, isopropyl, n-butyl, secondary-butyl, isobutyl, tertiary butyl, n-pentyl, n-hexyl, n-heptyl, n-octyl, n-nonyl, n-decyl, and the like.

"Aryl" means an aromatic radical which is a phenyl group or a phenyl group substituted by one to three substituents selected from the group consisting of alkyl of from one to three carbon atoms, halogen, and nitro.

"Halogen" is iodine, bromine, chlorine, and fluorine.

"Alkali metal" is a metal in Group IA of the periodic table and includes, for example, lithium, sodium, potassium, and the like.

"Alkaline-earth metal" is a metal in Group IIA of the periodic table and includes, for example, calcium, barium, strontium, magnesium and the like.

"Leaving group" is halogen, $R^3-SO_3-$ wherein $R^3$ is alkyl of from one to four carbon atoms or aryl or $R_3{}^4\oplus N-$ wherein $R^4$ is alkyl of from one to four carbon atoms or benzyl.

The process of the present invention is a new, improved, economical, and commercially feasible method for preparing (5R)-1,1-dimethylethyl 6-cyano-5-hydroxy-3-oxo-hexanoate. The process of the present invention is outlined in the following Scheme I:

chlorine, bromine, iodine, fluorine, and the like, $R^3-SO_3-$ wherein $R^3$ is alkyl of from one to four carbon atoms or aryl such as, for example, para-toluenesulfonyloxy, methanesulfonyloxy, and the like or $R_3{}^4\oplus N-$ wherein $R^4$ is alkyl of from one to four carbon atoms or benzyl, and the like, and R is as defined above with a compound of Formula IV wherein $R^1$ is tetraalkylammonium, silver, copper (I), copper (II), an alkali metal or an alkaline earth metal, and a solvent such as, for example, ethanol, dimethylformamide, tetrahydrofuran, water, mixtures thereof, for example, ethanol-water, dimethylformamide-water, tetrahydrofuran-water, and the like at about 0° C. to about the reflux temperature of the solvent to afford a compound of Formula II. Preferably, the reaction is carried out wherein R is ethyl in a compound of Formula II in ethanol-water at about 15° C. to 20° C.

Optionally, a compound of Formula II is prepared by treating a compound of Formula VI wherein R is as defined above with a compound of Formula IV in a solvent at about 0° C. to about the reflux temperature of the solvent to afford a compound of Formula II. Preferably, the reaction is carried out wherein R is ethyl in a compound of Formula II in ethanol-water at about 15° C. to 20° C.

The compound of Formula I is prepared by treating a compound of Formula II with a compound of Formula III wherein $R^2$ is zinc, magnesium, lithium, sodium, or potassium in an aprotic solvent such as, for example, tetrahydrofuran, hexanes, diethyl ether, tertiary butyl methyl ether, mixtures thereof, for example, tetrahydrofuran-hexanes, tetrahydrofurandiethyl ether, tetrahydrofuran-tertiary butyl methyl ether, hexanes-diethyl ether, hexanes-tertiary butyl methyl ether, diethyl ether-tertiary butyl methyl ether, and the like at about −80° C. to about 10° C. for about 1 minute to about 4 hours, in the presence of additional compound of Formula III or a base such as, for example, lithium

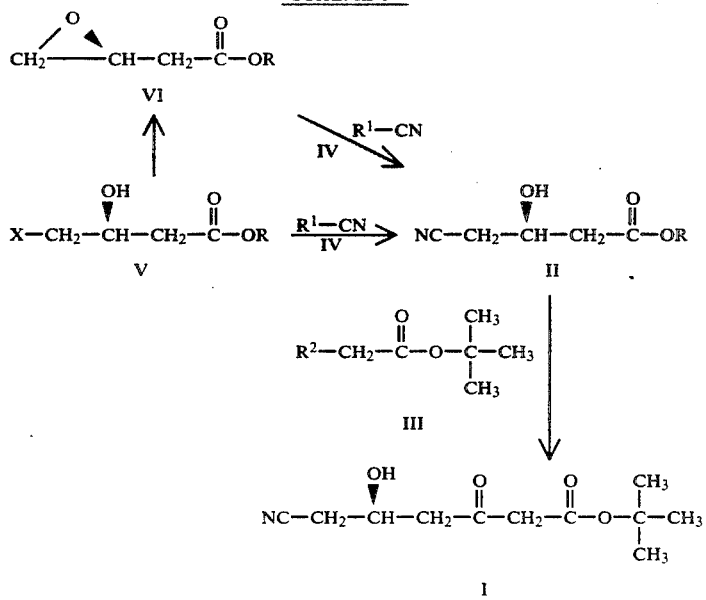

A compound of Formula II wherein R is alkyl of from one to ten carbon atoms, allyl, or benzyl is prepared by treating a compound of Formula V wherein X is a leaving group such as, for example, halogen such as diisopropylamide and the like, and optionally in the presence of added salt such as, for example, zinc chloride, lithium chloride, cerium chloride and the like to afford the compound of Formula I. Preferably, the reaction is carried out in tetrahydrofuran at about −20° C. to about −30° C. for about 5 to about 30 minutes.

A compound of Formula III is prepared by treating tertiary butyl acetate with a strong base such as, for example, lithium diisopropylamide. Alternatively, a compound of Formula III is prepared from, for example, 2-chloro tertiary-butyl acetate or 2-bromo tertiary butyl acetate by reaction with a zero valent metal such as zinc, magnesium or lithium using conventional methodology.

A compound of Formula V wherein X is halogen is prepared using conventional methodology from known starting materials. Thus, a compound of Formula V wherein X is bromo is prepared according to the methodology disclosed by Bock, K., et al, *Acta Chemica Scandinavica* B37, pages 341-344 (1983). This compound may be prepared by other conventional means. Additionally, a compound of Formula V wherein X is chloro may be prepared using the methodology disclosed by Kitamura, M., et al, *Tetrahedron Letters*, Volume 29, pages 1555-1556 (1988). A compound of Formula V wherein X is iodo is prepared from a compound of Formula V wherein X is chloro using conventional methodology.

A compound of Formula V wherein X is $R^3$—SO$_3$— is prepared using conventional methodology from known starting materials. Thus, a compound of Formula V wherein X is para-toluenesulfonyloxy or methanesulfonyloxy is prepared by reacting (S) 3,4-dihydroxybutanoic acid, ethyl ester which is prepared by the method of Saito, S., et al, *Chemistry Letters*, pages 1389-1392 (1984) with respectively para-toluenesulfonyl chloride or methanesulfonyl chloride.

A compound of Formula V wherein X is $R_3^4 \oplus N$— is prepared from a compound of Formula V wherein X is bromo using the methodology disclosed by Bock, K., et al, *Acta Chemica Scandinavica* B37, pages 341-344 (1983).

A compound of Formula VI is prepared from a compound of Formula V using conventional methodology.

A compound of Formula IV is either known or capable of being prepared by methods known in the art.

U.S. Pat. No. 5,003,080 discloses the use of (5R)-1,1-dimethylethyl 6-cyano-5-hydroxy-3-oxo -hexanoate in the preparation of (4R-cis)-1,1-dimethylethyl 6-cyanomethyl-2,2-dimethyl-1,3-dioxane -4-acetate, which in turn is used to prepare (4R-cis) -1,1-dimethylethyl 6-(2-aminoethyl-2,2-dimethyl-1,3-dioxane-4-acetate, which in turn is used to prepare (2R-trans)-5-(4-fluorophenyl)-2-(1-methylethyl)-N,4-diphenyl-1-[2-(tetrahydro-4-hydroxy-6-oxo-2H-pyran-2-yl)ethyl]-1H-pyrrole-3-carboxamide or the salt of the hydroxy acid, [R-(R*,R*)]-2-(4-fluorophenyl)-β,δ-dihydroxy-5-(1-methylethyl)-3-phenyl-4-[(phenylamino)carbonyl]-1H-pyrrole-1-heptanoic acid calcium salt (2:1), corresponding to the opened lactone ring of the aforementioned compound which is disclosed in U.S. Pat. Nos. 4,647,576 and 4,681,893 as a useful hypolipidemic and hypocholesterolemic agent.

The following examples are illustrative to show the present process, the preparation of starting materials, and the use of (5R)-1,1 dimethylethyl 6-cyano-5-hydroxy-3-oxo-hexanoate obtained by the present process to prepare (4R-cis)-1,1-dimethylethyl 6-cyanomethyl-2,2-dimethyl-1,3-dioxane-4-acetate which in turn is used to prepare the key intermediate, (4R -cis)-1,1-dimethylethyl 6-(2-aminoethyl)-2,2-dimethyl1,3-dioxane-4-acetate, in the synthesis of (2R-trans)-5-(4-fluorophenyl)-2-(1-methylethyl)-N,4-diphenyl-1-[2-(tetrahydro-4-hydroxy-6-oxo-2H pyran-2-yl)ethyl]-1H-pyrrole-3-carboxamide or the salt of the hydroxy acid, [R-(R*,R*)]-2-(4-fluorophenyl)-β,δ-dihydroxy-5-(1-methylethyl)-3-phenyl-4-[(phenylamino)carbonyl]-1H -pyrrole-1-heptanoic acid calcium salt (2:1), corresponding to the opened lactone ring of the aforementioned compound useful as a hypolipidemic and hypocholesterolemic agent.

EXAMPLE 1

(5R)-1,1-Dimethylethyl 6-cyano-5-hydroxy-3-oxo -hexanoate

Step A: Preparation of (R)-4-Cyano-3-hydroxybutyric acid, ethyl ester

Method A

To a 50 gallon reactor containing a solution of 2.2 kg (44 mol) of sodium cyanide dissolved in 40 L of demineralized water is added 7 kg (33 mol) of (S) 4-bromo-3-hydroxybutyric acid, ethyl ester dissolved in 8 L of ethanol. The reaction mixture is stirred for 16 hours at room temperature. Ethyl acetate, 65 L, is added and the mixture agitated and the layers are allowed to separate. The lower aqueous layer is transferred to a 50 gallon vessel containing 2.5 kg of sodium chloride and 65 L of ethyl acetate and the mixture agitated and the layers allowed to separate and the lower aqueous layer is cut off. The organic layers are combined and concentrated in vacuo. The residue is distilled to afford 3.1 kg of the title compound; bp 110°-125° C. 0.5 mm Hg; optical rotation $[\alpha]_D^{25} = -33.1°$ (C=1.08, chloroform); Vapor Phase Chromatography (VPC): 30 meter DB-5 capillary column 100 (2) to 280 (15) at 15° C./minute, 7.28 minutes retention time, 95.6% area; $^1$H-NMR: (deuterated chloroform (CDCl$_3$) 1.29 (3H, t), 2.64 (4H, m), 3.84 (1H, bs), 4.18 (2H, quartet), 4.36 (1H, quintet).

Method B

To a 100 mL round bottom flask containing 3.5 g (24 mmol) of (S) 3,4-dihydroxybutyric acid, ethyl ester (prepared by the method of Saito, S., et al, *Chemistry Letters*, pages 1389-1392 (1984)) dissolved in 40 mL of methylene chloride is added 7 mL of triethylamine. The reaction mixture is cooled to 10° C., para-toluenesulfonyl chloride (3.7 g, 20 mmol) is added, and the reaction stirred for 16 hours at room temperature. Water, 50 L, is added followed by 5 mL of concentrated aqueous hydrochloric acid solution. After agitation, the lower layer is separated and washed three times with 100 mL of water, then concentrated in vacuo to an oil. The crude oil is slurried in 16 mL of ethanol and 20 mL of water and 1.2 g of sodium cyanide is added to the stirred solution. After stirring at room temperature for 16 hours, the reaction mixture is diluted by the addition of 50 mL of ethyl acetate and 2 g of sodium chloride. The mixture is thoroughly agitated and the layers allowed to separate. The lower aqueous layer is rewashed with 50 mL of ethyl acetate. The organic layers are combined and concentrated in vacuo. The crude product is dissolved in 60 mL of water and the aqueous layer washed with 10 mL of toluene. The aqueous layer is then extracted by adding 10 g of sodium chloride and 100 mL of ethyl acetate, agitating vigorously and separating the top organic layer. The organic layer is concentrated in vacuo and the product is purified by column chromatography on flash silica gel, eluting with 1:1 hexane:ethyl acetate followed by vacuum distillation to afford 1.0 g of the title compound; b.p. 110°-125° C. @ 0.5 mm Hg. Vapor phase chromatography (VPC): 30 meter DB-5 capillary column 100(2) to 280(15) at 15° C./min. 7.28 minutes retention time, 85.6% area. GC/MS m/e 157, 130, 112, 94, 71, 43.

Step B: Preparation of (5R)-1,1-Dimethylethyl 6-cyano-5-hydroxy 3-oxo-hexanoate

Method A

To a stirred −50° C. solution of lithium diisopropylamide (100 kg of 2 M) in tetrahydrofuranheptane is added tertiary-butyl acetate (30 kg, 255 mol) followed by a rinse of 3 kg of tetrahydrofuran and the mixture is stirred at −45° C. to −5° C. for 50 minutes. (R)-4-cyano-3-hydroxybutyric acid, ethyl ester (10 kg, 64 mol) as a solution in 30 kg of tetrahydrofuran is then added to the previous mixture. The reaction mixture is stirred for 30 minutes at −5° C. to −30° C., and transferred to 240 L of 0° C. 2.8 N aqueous hydrochloric acid solution. The aqueous layer is extracted with 50 kg of ethyl acetate, the aqueous layer is separated and reextracted with 36 kg of ethyl acetate, the extracts are combined and concentrated in vacuo to afford crude (5R)-1,1-dimethylethyl 6-cyano-5-hydroxy-3-oxo -hexanoate which is not isolated. A small sample is purified by column chromatography on flash silica gel eluting with 1:1 hexane:ethyl acetate. $^1$H—NMR: (CDCl$_3$) 1.48 (9H, s), 2.61 (2H, m), 2.88 (2H, d), 3.43 (2H, s), 3.58 (1H, bs), 4.40 (1H, m). MS:(EI) m/e, (%): 229 (3), 228(26),173(10), 172(100), 154(62), 112(30), 59(50), 57(77).

Method B

To a stirred −50° C. solution of tertiary-butyl acetate (60 mL, 0.44 mol), (R)-4-cyano-3-hydroxybutyric acid, n-butyl ester (20 g, 0.11 mol) and 150 mL tetrahydrofuran is added lithium diisopropylamide (300 mL of 1.5 M) in tetrahydrofuran over 15 minutes and the mixture is stirred at −45° C. to −50° C. for 90 minutes. To this solution is added 700 mL of 5% aqueous hydrochloric acid solution along with 300 mL of ethyl acetate. The aqueous layer is separated and the remaining top layer washed with aqueous sodium chloride solution. The organic layer is then concentrated in vacuo to afford crude (5R)-1,1-dimethylethyl 6-cyano-5-hydroxy-3-oxo-hexanoate which is not isolated, and is carried on to (4R-cis)-1,1-dimethylethyl 6-cyanomethyl-2,2-dimethyl -1,3-dioxane-4-acetate as described in Example 2. TLC: R$_f$=0.15 (1:1 ethyl acetate: hexanes) on a Kieselgel 60 F$_{254}$ 0.254 mm silica thin layer plate.

EXAMPLE 2

(4R-Cis)-1,1-dimethylethyl 6-cyanomethyl-2,2-dimethyl -1,3-dioxane-4-acetate

Step A: Preparation of [R-(R*,R*)]-1,1-Dimethylethyl 6-cyano-3,5-dihydroxyhexanoate Crude (5R)-1,1-dimethylethyl 6-cyano-5-hydroxy-3-oxo-hexanoate (Example 1), approximately 52 mol, is dissolved in 90 L of tetrahydrofuran and 19 L of methanol under a nitrogen atmosphere. This solution is cooled to −85° C. and 24 L of a 50% solution of methoxydiethylborane in tetrahydrofuran is added. The reaction is cooled to −97° C. and 3.6 kg (126 mol) of sodium borohydride is added in 0.2 kg portions over 3 hours. The reaction is maintained between −93° C. and −85° C. for 5 hours and allowed to warm to room temperature and stand for 10 hours under a nitrogen atmosphere. The reaction is quenched by the addition of 7.5 L (118.5 mol) of acetic acid and concentrated by vacuum distillation to an oil. The residue is dissolved with 40 L of methanol, concentrated by vacuum distillation, redissolved with 44 L of methanol and reconcentrated by vacuum distillation to give a brown oil. This oil is taken up in 90 L of ethyl acetate and washed with 30 L of deionized water. The ethyl acetate solution is concentrated by vacuum distillation to give the title compound, [R-(R*,R*)]-1,1-dimethylethyl 6-cyano-3,5-dihydroxyhexanoate, which is used without further purification.

Step B: Preparation of (4R-Cis)-1,1-dimethylethyl 6-cyanomethyl-2,2-dimethyl-1,3-dioxane-4-acetate Crude [R-(R*,R*)]-1,1-dimethylethyl 6-cyano-3,5-dihydroxyhexanoate (approximately 50 mol), is dissolved in 67.5 L of 2,2 dimethoxypropane and 38.0 L of acetone. Methanesulfonic acid (167 mL) is added, and the solution is stirred for 2 hours at room temperature. After the addition of 50 L of aqueous sodium bicarbonate and 80 L of ethyl acetate, the reaction is agitated, the layers separated, and the organic layer diluted with 80 L of hexane. The organic layer is washed two times with 100 L of water. After concentration by vacuum distillation, the residue is dissolved in 80 L of warm hexane. Crystals form upon cooling and provide 10.1 kg of product as an off-white solid after collection by filtration and drying. This material is recrystallized by dissolving in 80 L of heptane by warming to 50° C., cooling slowly to 10° C., and collecting the product by filtration. After drying, 9.1 kg of (4R-cis)-1,1-dimethylethyl 6-cyanomethyl-2,2-dimethyl-1,3-dioxane-4-acetate is obtained as an off-white solid (mp 64.7°-68° C.) with acceptable IR, NMR, C-NMR, and analysis. 200 MHz NMR (CDCl$_3$) δ 1.36 (m, 1H), 1.42 (s, 3H), 1.49 (s, 9H), 1.50 (s, 3H), 1.79 (dt, 1H, J=2.5 Hz, J =12.1 Hz), 2.40 (dd, 1H, J=6.2 Hz, J=15.4 Hz), 2.5-2.7 (m, 1H), 2.55 (d, 2H, J=6.1 Hz), 4.18 (m, 1H), 4.32 (m, 1H).

$^{13}$C-NMR (CDCl$_3$, 50 MHz) δ 19.74, 25.09, 28.24, 29.88, 35.58, 42.50, 65.20, 65.81, 80.87, 99.48, 116.68, 169.75.

GC/MS m/e 254, 198, 154, 138, 120, 59, 57, 43, 41.

Fourier Transform Infrared Spectroscopy (FTIR) (KBr) 941.4, 1116.2, 1154.8, 1188.3, 1257.7, 1293.7, 1309.1, 1368.3, 1725.8, 2361.1, 2983.5, 2996.4 cm$^{-1}$.

EXAMPLE 3

Preparation of (4R-Cis)-1,1-dimethylethyl 6-(2-aminoethyl)-2,2-dimethyl 1,3 dioxane-4 acetate A solution of (4R-cis)-1,1 dimethylethyl 6-cyanomethyl-2,2-dimethyl-1,3-dioxane-4-acetate (Example 2), 8.2 kg (30.5 mol) in 100 L of methanol containing 15 kg of anhydrous ammonia is reacted with hydrogen gas under 50 pounds per square inch (psi) at 30° C. in the presence of a slurry of 8 kg of Raney nickel doped with 1% molybdenum. After 6 hours, uptake of hydrogen has ceased, the mixture is cooled to 20° C., the atmosphere is vented and exchanged for nitrogen, and the slurry is filtered, concentrated by distillation and distilled under vacuum to give 7.8 kg of 96% pure (4R-cis)-1,1-dimethylethyl 6-(2-aminoethyl)-2,2-dimethyl-1,3-dioxane-4-acetate as a clear oil; bp 125°-135° C.

@0.5 mm Hg. 200 MHz $^1$H-NMR (CDCl$_3$) 1.0–1.2 (m, 1H), 1.22 (s, 3H), 1.31 (s, 12H), 1.35–1.45 (m, 3H), 2.15 (dd, 1H, J=15.1 Hz, J=6.2 Hz), 2.29 (dd, 1H, J=15.1Hz, J=7.0 Hz), 2.66 (t, 2H, J=6.6 Hz), 3.82 (m, 1H), 4.12 (m, 1H).

$^{13}$C-NMR (CDCl$_3$, 50 MHz), δ 19.60, 27.96, 30.00, 36.50, 38.25, 39.79, 42.61, 66.08, 67.18, 80.21, 98.35, 169.82.

GC/MS m/e 202, 200, 173, 158, 142, 140, 114, 113, 100, 99, 97, 72, 57.

FTIR (neat) 951.6, 1159.9, 1201.1, 1260.3, 1314.3, 1368.3, 1381.2, 1731.0, 2870.3, 2939.8, 2980.9, 3382.2 cm$^{-1}$.

EXAMPLE 4

(±)4-Fluoro-α-[2-methyl-1-oxopropyl]-γ-oxo-N,β-diphenylbenzenebutaneamide mixture of [R-(R*,R)], [R-(R*,S*)], [S-(R*,R*)] and [S-(R*,S*)] isomers

Step A: Preparation of 4-Methyl-3-oxo-N-phenyl-2-(phenylmethylene)pentanamide A suspension of 100 kg of 4 methyl-3-oxo-N -phenyl-pentanamide (Example A) in 660 kg of hexanes is treated with agitation under nitrogen with 8 kg of β-alanine, 47 kg of benzaldehyde, and 13 kg of glacial acetic acid. The resulting suspension is heated to reflux with removal of water for 20 hours. An additional 396 kg of hexanes and 3 kg of glacial acetic acid is added and reflux continued with water removal for 1 hour. The reaction mixture is cooled to 20° C. to 25° C., and the product is isolated by filtration. The product is purified by slurring in hexanes at 50° C.–60° C., cooling, and filtration. The product is slurred twice with water at 20° C. to 25° C., filtered, and dried in vacuo to yield 110 kg of 4-methyl-3-oxo-N-phenyl-2-(phenylmethylene)pentanamide, mp 143.7–154.4° C.

Vapor Phase Chromatography (VPC): 30 meter DB-5 capillary column 50° C. to 270° C. at 15° C./min. 19.33 min., 99.7% (area).

Gas Chromatography/Mass Spectrometry (GC/MS): M/Z 293 [M]+.

Nuclear Magnetic Resonance ($^1$H-NMR): (CDCl$_3$) δ1.16 (6H, d), 3.30 (1H, quin.), 7.09 (1H, m), 7.28 (5H, m), 7.49 (5H, m), 8.01 (1H, brs).

Step B: Preparation of (±) 4-Fluoro-α-2-methyl-1-oxopropyl]γ-oxo-N-β-diphenylbenzenebutaneamide mixture of [R-(R*,R*)], [R-(R*,S*)], S-(R*,R*)] and [S (R*,S*)] isomers A solution of 17.5 kg of 3-ethyl-5-(2-hydroxyethyl)-4-methylthiazolium bromide in 300 L of anhydrous ethanol is concentrated by distillation of 275 L of the ethanol. Under an argon atmosphere, 100 kg (340 mol) of 4methyl-3-oxo-N-phenyl-2-(phenylmethylene)pentamide, 47.5 L (340 mol) of triethylamine, and 40 L (375 mol) of 4-fluorobenzaldehyde are added. The resulting solution is stirred and heated at 75° C. to 80° C. for 23 hours. The slurry is dissolved in 600 L of isopropanol at 80° C. The resulting solution is slowly cooled and the product is isolated by filtration. Washing the precipitate with isopropanol and drying in vacuo affords 99 kg of (±) 4-fluoro-α-[2-methyl-1-oxopropyl]-γ-oxo-N-β-diphenylbenzenebutaneamide mixture of [R-(R*,R*)], [R-(R*, S*)], [S-(R*,R*)] and [S-(R*,S*)] isomers; mp 206.8° C.–207.6° C.

$^1$H—NMR (CDCl$_3$) δ1.03 (3H, d), 1.22 (3H, d), 2.98 (1H, quin.), 4.91 (1H, d, J=11 Hz). 5.51 (1H, d, J=11 Hz), 6.98–7.43 (12H, m), 8.17 (2H, dd), 9.41 (1H, brs).

High Pressure Liquid Chromatography (HPLC): (Acetonitrile:tetrahydrofuran:water) (40:25:55) Econosil C$_{185\mu}$25 cm 1.0 mL/min 254 nm 16.77 min 99.2% (area).

EXAMPLE 5

(2R-Trans)-5-(4-fluorophenyl)-2-(1 methylethyl)-N,4-diphenyl-1-[2-(tetrahydro 4-hydroxy 6-oxo-2H-pyran-2-yl)ethyl]-1H-pyrrole-3-carboxamide

Method A

Step A: Preparation of (4R-cis)-1,1-dimethylethyl 6-[2[2-(4-fluorophenyl)-5 (1-methylethyl)-3-phenyl-4[(phenylamino)carbonyl]-1H-pyrrol-1-yl]ethyl]-2,2-dimethyl-1,3-dioxane-4-acetate A solution of (4R-cis)-1,1-dimethylethyl 6-(2-amino-ethyl-2,2-dimethyl-1,3-dioxane-4-acetate, (Example 3) 1.36 g (4.97 mmol), and (±) 4-fluoro-α-[2-methyl-1-oxopropyl]-γ-oxo-N-β-diphenyl -benzenebutaneamide mixture of [R-(R*,R*)], [R -(R*,S*)], [S-(R*,R*)] and [S-(R*,S*)] isomers, (Example 4) 1.60 g (3.83 mmol), in 50 mL of heptane:toluene (9:1) is heated at reflux for 24 hours. The solution is cooled slightly and 15 mL of 2-propanol added. The mixture is allowed to cool to 25° C. and filtered to give 1.86 g of (4R-cis)-1,1-dimethylethyl 6-[2[2-(4-fluorophenyl)-5-(1-methyl -ethyl)-3-phenyl-4-[(phenylamino)carbonyl]-1H-pyrrol-1-yl]ethyl]-2,2-dimethyl-1,3-dioxane-4-acetate as a yellow solid.

$^1$H-NMR (CDCl$_3$, 200 MHz) δ 1–1.7 (m, 5H), 1.30 (s, 3H), 1.36 (s, 3H), 1.43 (s, 9H), 1.53 (d, 6H, J=7.1 Hz), 2.23 (dd, 1H, J=15.3 Hz, J=6.3 Hz), 2.39 (dd, 1H, J=15.3 Hz, J=6.3 Hz), 3.5–3.9 (m, 3H), 4.0–4.2 (m, 2H), 6.8–7.3 (m, 14H).

$^{13}$C-NMR (CDCl$_3$, 50 MHz) δ 19.69, 21.60, 21.74, 26.12, 27.04, 28.12, 29.95, 36.05, 38.10, 40.89, 42.54, 65.92, 66.46, 80.59, 98.61, 115.00, 115.34, 115.42, 119.52, 121.78, 123.36, 126.44, 128.21, 128.31, 128.52, 128.75, 130.43, 133.01, 133.17, 134.69, 138.38, 141.47, 159.72, 164.64, 169.96.

Step B: Preparation of (2R-Trans)-5-(4-fluorophenyl) -2-(1-methylethyl)-N,4-diphenyl-1-[2-(tetrahydro-4-hydroxy-6-oxo-2H-pyran-2-yl)ethyl]-1H-pyrrole-3-carboxamide (4R-Cis)-1,1-dimethylethyl 6-[2[2-(4-fluoro-phenyl)-5-(1-methylethyl)-3-phenyl-4-[(phenylamino) -carbonyl]-1H-pyrrol-1-yl]ethyl]2,2-dimethyl-1,3-dioxane-4-acetate, 4.37 g (6.68 mmol), is dissolved in 200 mL of tetrahydrofuran and 15 mL of 10% hydrochloric acid solution is added, and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for 3 hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred 2 hours, concentrated in vacuo, and dissolved in 3.0 mL of toluene. (2R-Trans)-5-(4-fluorophenyl)-2-(1-methyl -ethyl)-N,4-diphenyl-1-[2-(tetrahydro-4-hydroxy-6-oxo -2H-pyran-2-yl)ethyl]-1H-pyrrole-3-carboxamide (3.01 g) is isolated in two crops.

Method B

A solution of (4R-cis) 1,1-dimethylethyl 6-(2-aminoethyl-2,2-dimethyl-1,3-dioxane-4-acetate, (Example 3) 2.56 g (9.36 mmol), and (±) 4-Fluoro-α-[2-methyl-1 -oxopropyl]-γ-oxo-N-β-diphenylbenzenebutane -amide mixture of [R-(R*,R*)], [R-(R*,S*)], [S-(R*,R*)] and [S-(R*,S*)]isomers (Example 4), 3.00 g (7.20 mmol), in 60 mL of heptane:toluene (9:1) is heated at reflux for 24 hours. The solution is cooled and poured into 300 mL of tetrahydrofuran and 150 mL of saturated ammonium chloride in water. The layers are separated and the organic layer is added to 15 mL of 10% hydrochloric acid solution and the solution is stirred for 15 hours. To this solution is added sodium hydroxide (3.6 g) and the mixture is stirred for 30 hours. The reaction is stopped by adding 150 mL of water, 90 mL of hexane, and separating the layers. The aqueous layer is acidified with dilute hydrochloric acid solution, stirred for 3 hours and extracted with 150 mL of ethyl acetate. A drop of concentrated hydrochloric acid is added to the ethyl acetate solution and the solution is allowed to stand 18 hours. The solution is concentrated in vacuo and the concentrate is redissolved in 50 mL of ethyl acetate and treated with one drop of concentrated hydrochloric acid. The solution is stirred 2 hours, concentrated in vacuo, and dissolved in 3.0 mL of toluene. (2R-Trans)-5-(4-fluorophenyl)-2-(1-methylethyl)-N,4-diphenyl-1-[2-(tetrahydro-4-hydroxy -6-oxo-2H-pyran-2-yl)ethyl]-1H-pyrrole-3-carboxamide (2.92 g) is isolated in two crops.

PREPARATION OF STARTING MATERIALS

EXAMPLE A

4-Methyl-3-oxo N phenylpentamide

A three-necked, 12-L round-bottom flask equipped with a mechanical stirrer, a thermometer, and set up for distillation is charged with 2.6 L of toluene, 1.73 kg (12 mol) of methyl 4-methyl-3-oxopentanoate and 72 g (1.18 mol) of ethylenediamine. The mixture is heated to 80° C. and charged with 0.49 kg of aniline. The mixture is brought to reflux and distillation started. After 40 minutes a further 0.245 kg of aniline is charged and at 40-minute intervals a further two portions of aniline (0.245 and 0.25 kg) are charged. Distillation is continued for a further one to five hours until a total of 985 mL of solvent is removed. The solution is stirred at room temperature for 16 hours and a further 550 mL of solvent is removed by vacuum distillation (using approximately 85 mm Hg). The mixture is cooled and 2 L of water is charged to provide an oil. The mixture is warmed to 40° C. and a further 1.0 L of water is charged. Seven hundred milliliters of toluene-water mixture is removed by vacuum distillation (approximately 20 mm Hg). Two liters of water is charged and the mixture is allowed to stand for 10 days. The product is isolated by filtration and washed with three portions of hexane. Drying in vacuo gives 1.7 kg of 4-methyl-3-oxo-N-phenylpentanamide as a hydrate; mp 46.5° C.–58.8° C.

HPLC: 98.8%—retention time 3.56 minutes. 65/35 acetonitrile/water on a dry basis.

VPC: 87.6%—retention time 12.43 minutes, also 10.8% aniline (decomposition).

We claim:

1. A process for the preparation of the compound of Formula I.

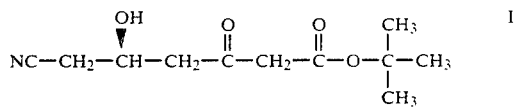

which comprises:

(a) treating a compound of Formula V

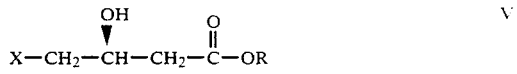

wherein R is alkyl of from one to ten carbon atoms, allyl, or benzyl and X is a leaving group with a compound of Formula IV

wherein $R^1$ is a tetraalkylammonium, silver, copper (I), copper (II), an alkali metal or an alkaline earth metal in a solvent at about 0°C. to about the reflux temperature of the solvent to afford a compound of Formula II

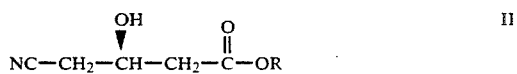

wherein R is as defined above; or optionally treating a compound of Formula VI

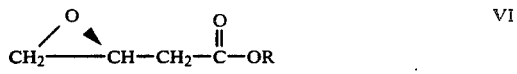

wherein R is as defined above with a compound of Formula IV in a solvent at about 0° C. to about the reflux temperature of the solvent to afford a compound of Formula II; and (b) treating a compound of Formula II with a compound of Formula III

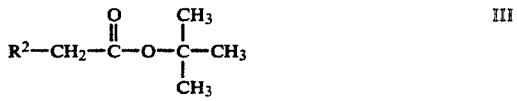

wherein $R^2$ is zinc, magnesium or lithium and a solvent at about −80° C. to about room temperature to afford the compound of Formula I.

2. A process according to claim 1 wherein the solvent in Step (a) is selected from the group consisting of a mixture of ethanol-water, a mixture of dimethylformamide-water, and a mixture of tetrahydrofuran-water.

3. A process according to claim 1 wherein a compound of Formula IV in Step (a) is selected from the group consisting of tetraalkylammonium cyanide, silver cyanide, cuprous cyanide, cupric cyanide, sodium cyanide, and potassium cyanide.

4. A process according to claim 3 wherein the compound of Formula IV is selected from the group consisting of sodium cyanide and potassium cyanide.

5. A process according to claim 1 wherein the compound of Formula V in Step (a) is selected from the group consisting of (S) 4-bromo-3-hydroxybutyric acid, ethyl ester, (S) 4-bromo-3-hydroxybutyric acid, methyl ester, (S) 4-bromo-3-hydroxybutyric acid, n-butyl ester, (S) 4-methanesulfonyloxy-3-hydroxybutyric acid, ethyl ester, (S) 4-methanesulfonyloxy-3-hydroxybutyric acid, methyl ester, (S) 4-methanesulfonyloxy-3-hydroxybutyric acid, n-butyl ester, (S) 4-para-toluenesulfonyloxy-3-hydroxybutyric acid, ethyl ester, (S) 4-paratoluenesulfonyloxy-3-hydroxybutyric acid, methyl ester, and (S) 4-para-toluenesulfonyloxy-3-hydroxybutyric acid, n-butyl ester.

6. A process according to claim 5 wherein the compound of Formula V is selected from the group consisting of (S) 4-bromo-3-hydroxybutyric acid, ethyl ester, and (S)-4-para-toluenesulfonyloxy-3-hydroxybutyric acid, ethyl ester.

7. A process according to claim 1 wherein the compound of Formula III is lithium tertiary butyl acetate.

8. A process according to claim 1 wherein the solvent in Step (b) is selected from the group consisting of tetrahydrofuran, hexanes, diethyl ether, tertiary butyl methyl ether, tetrahydrofuran-hexanes, tetrahydrofuran-diethyl ether, tetrahydrofuran-tertiary butyl methyl ether, hexanes-diethyl ether, hexanes-tertiary butyl methyl ether, and diethyl ether-tertiary butyl methyl ether.

* * * * *